United States Patent [19]

Jimenez et al.

[11] Patent Number: 5,486,509
[45] Date of Patent: Jan. 23, 1996

[54] METHOD OF PREVENTING AND TREATING CHEMOTHERAPY-INDUCED ALOPECIA

[75] Inventors: Joaquin J. Jimenez; Adel A. Yunis, both of Miami, Fla.

[73] Assignee: University of Miami, Miami, Fla.

[21] Appl. No.: 250,646

[22] Filed: May 27, 1994

Related U.S. Application Data

[63] Continuation of Ser. No. 903,829, Jun. 24, 1992, abandoned, which is a continuation-in-part of Ser. No. 810,412, Dec. 20, 1991, abandoned, which is a continuation-in-part of Ser. No. 786,788, Nov. 1, 1991, abandoned, which is a continuation-in-part of Ser. No. 722,500, Jun. 28, 1991, abandoned.

[51] Int. Cl.$^6$ .......................... A61K 31/59; C07C 401/00
[52] U.S. Cl. .......................... 514/167; 552/653; 514/880; 514/922
[58] Field of Search .............................. 424/45; 514/711, 514/12, 21, 167–171; 530/399; 552/653

[56] References Cited

U.S. PATENT DOCUMENTS

| | | | |
|---|---|---|---|
| Re. 33,107 | 11/1989 | Dikstein et al. | 514/46 |
| 3,711,602 | 1/1973 | Herschler | 424/45 |
| 4,863,902 | 9/1989 | Amagase et al. | 514/12 |
| 4,871,723 | 10/1989 | Makino et al. | 514/167 |
| 4,883,791 | 11/1989 | Pak et al. | 514/167 |
| 4,891,364 | 1/1990 | Kubodera et al. | 514/167 |
| 4,929,610 | 5/1990 | Meier et al. | 514/167 |
| 4,997,824 | 3/1991 | Popovtzer et al. | 514/170 |
| 5,039,671 | 8/1991 | Baggiolini et al. | 514/167 |
| 5,043,170 | 8/1991 | Borenstein et al. | 514/167 |
| 5,053,401 | 10/1991 | Matsumoto et al. | 514/167 |
| 5,063,221 | 11/1991 | Nishii et al. | 514/167 |
| 5,069,905 | 12/1991 | Lidor et al. | 424/423 |
| 5,102,870 | 4/1992 | Florine et al. | 514/12 |

FOREIGN PATENT DOCUMENTS

| | | |
|---|---|---|
| 9100271 | 9/1990 | WIPO . |
| 9009991 | 1/1991 | WIPO . |
| 9203414 | 3/1992 | WIPO . |

OTHER PUBLICATIONS

H. Reichel et al. Ann Rev. Med. 40:71–8 1989.

K. Katsuoka et al. Arch Dermatol Res 279:247–50 1987.

J. Darnell et al. "Molecular Cell Biology" Scientific American Books 1986 pp. 698, 845–848.

Review of Physiological Chemistry, 17th Ed. H. A. Harper et al. Lange Med. Pubs, Los Altos, 1979 p. 648.

Practical Dermatology, 4th Ed. I. B. Sneddon et al. Edward Arnold (Pub), London 1983 p. 193.

Jimenez et al, "Interleukin-1 protects from cystosine arabinoside-induced alopecia in the rat model", FASEB J., vol. 5, Issued Jul. 1991, pp. 2456–2458, entire document.

Hussein et al, "protection from Chemotherapy-induced alopecia in a rat model", Science, vol. 249, issued Sep. 28, 1990, pp. 1564–1566 entire document.

Jimenez et al, "Stimulated monocyte-conditioned media protect from cytosine arabinoside-induced alopecia in rat", Cancer Research, vol. 38–(4), Issued 1990, p. 973A, entire document.

Jimenez et al, "Protection from 1-D-arabinofuranosylcytosine-induced alopecia by epidermal growth factor and fibroblast growth factor in the rat model", Cancer Res., vol. 52, Issued 15 Jan. 1992), pp. 413–415, entire doc.

Becker, ed. Principles and Practice of Endocrinology and Metabolism, Lippincott Co., Phila. 1990, pp. 347–348.

G. P. M. Moore et al. J. Endocrinology 88:293–299, 1981.

Zinc Fingers and Vitamin D Resistance, The Lancet, Mar. 4, 1989, p. 478.

Feldman et al., Molecular and Cellular Endocrinology, 72 (1990) pp. 57–62.

*Primary Examiner*—Stephen G. Walsh
*Assistant Examiner*—Lorraine M. Spector
*Attorney, Agent, or Firm*—Morgan & Finnegan

[57] ABSTRACT

The present invention relates, in general, to a method of inhibiting alopecia, or hair loss, and, in particular, to a method of inhibiting alopecia induced by chemotherapeutic agents. The invention further relates to a composition suitable for use in such a method. Active agents for use in the above method include proteinaceous growth factors, such as EGF, and/or vitamin $D_3$ or metabolites thereof.

37 Claims, 9 Drawing Sheets

5,486,509

METHOD OF PREVENTING AND TREATING CHEMOTHERAPY-INDUCED ALOPECIA

This is a continuation of application Ser. No. 07/903,829, filed on Jun. 24, 1992, now abandoned, which is CIP of Ser. No. 07/810,412 filed Dec. 20, 1991, now abandoned, which is a CIP of Ser. No. 07/786,788, filed Nov. 1, 1991, now abandoned, which is a CIP of Ser. No. 07/722,500, filed Jun. 28, 1991, now abandoned.

TECHNICAL FIELD

The present invention relates, in general, to a method of preventing or treating alopecia induced by chemotherapeutic agents.

BACKGROUND

Alopecia is a common and distressing side effect of many chemotherapeutic agents and for which there is currently no effective preventive measure. In a recent study, thirty-five of forty-six patients receiving chemotherapy ranked alopecia as more important than vomiting (Tierney et al, B. J. Cancer, 62:527–528, 1990).

Recently, using the young rat model, Applicants demonstrated that ImuVert, a biologic response modifier prepared from the bacterium *Serratia marcescens*, protected the animals from alopecia induced by cytosine arabinoside or adriamycin (Hussein et al, Science 249: 1564–1566, 1990). In subsequent studies, similar protection from ARA-C-induced alopecia was observed from recombinant interleukin-1 (IL-1) beta (Jimenez et al FASEB J. 1991).

The present invention provides an independent method of preventing and treating chemotherapy-induced alopecia. This method involves the use of a growth factor, such as epidermal growth factor (EGF) or fibroblast growth factor (FGF). It should be noted that, as far as Applicants are aware, ImuVert has not been shown to stimulate the production of EGF or FGF, nor has it been proposed to stimulate such production.

The present invention also relates to the use of Vitamin $D_3$, or a metabolite thereof, alone or in combination with EGF to prevent or treat alopecia. Vitamin $D_3$ is absorbed after ingestion of fish liver oils or irradiated yeast. Plants and animal sources contain only the inactive vitamin D precursors, 7-dehydrocholesterol or ergosterol. 7-Dehydrocholesterol is stored in the skin and can be converted by sunlight into vitamin $D_3$. However, whether ingested or formed by ultraviolet irradiation in the skin, Vitamin D has to be transformed into active metabolites. Vitamin $D_3$ is converted to 25-hydroxycholecalciferol by liver enzymes. Then in the kidneys two compounds 1,25-dihydroxycholecalciferol and 24,25-dihydroxycholecalciferol are formed. The vitamin D active metabolites play an important role in the absorption of calcium from the intestinal tract, bone deposition and bone reabsorptiono 1,25-Dihydroxyvitamin $D_3$, an active metabolite of Vitamin $D_3$, has been shown to increase EGF receptors on breast cancer cells (Falette et al, Molec. and Cell. Endocrinol., 63 (1–2):189–198, 1989) and on a cell line established from rat calvaria (Petkovich et al, J. Biol. Chem. 262 (28): 13424–13428, 1987). However, as far as Applicants are aware, the effect of Vitamin $D_3$ or a metabolite thereof, on alopecia has not been shown or proposed.

SUMMARY OF THE INVENTION

It is a general object of the invention to provide a method of treating or preventing alopecia. It is a specific object of the invention to prevent or treat alopecia in patients undergoing treatment with chemotherapeutic agents, including cycle specific agents (such as cytosine arabinoside (ARA-C)) and non cycle specific agents (such as Cytoxan), individually or in combination.

Further objects and advantages of the invention will be clear from the description that follows.

DETAILED DESCRIPTION OF THE INVENTION

Figure 1:
FIG. 1 is a photograph of 10 rats from Experiment I, Table I (see below). All rats received ARA-C 50 mg/kg×7 days. Five rate on top received buffer solution s.c. Five rats on bottom received murine EGF 2 µg s.c. daily×7 days.

The present invention relates generally to a method of preventing or reducing alopecia, particularly in patients undergoing chemotherapy. Applicants have shown that a growth factor, such as EGF, and Vitamin $D_3$ appear to render the hair follicle resistant to the toxic effect of chemotherapeutic agents thus preventing hair loss.

In one embodiment of the present method, a growth factor is administered to a patient undergoing chemotherapy in an amount sufficient to prevent or reduce the hair loss that normally accompanies this treatment regimen.

Growth factors suitable for use in the present method include EGF, FGF, transforming growth factors (TGF), and platelet-derived growth factor (PDGF). The growth factors can be derived from natural sources (for example, human tissue or rodent tissue); however, recombinant production is preferred as large quantities can be produced at relatively low cost. Chemically synthesized factors can also be used. The use of portions or derivatives of growth factors, such as EGF and FGF, is also contemplated as long as those portions or derivatives can effect the same result observed with the factor itself.

In another embodiment of the present invention, Vitamin $D_3$ or metabolite, analog, derivative or structural variant thereof (for example 1,25-dihydroxy-16-ene-23-yne-cholecalciferol; 1 $\alpha$-hydroxyvitamin $D_3$; 1 $\alpha$-24-dihydroxyvitamin $D_3$, MC 903, etc.) is administered to a warm blooded animal, for example, a human, in an amount sufficient to prevent or reduce the hair loss or stimulate hair growth. Hair loss treatable or preventable using vitamin $D_3$ can be due to chemotherapy or other cause. Examples of Vitamin $D_3$ metabolites suitable for use in the present method include, but are not limited to, 1,25-dihydroxyvitamin $D_3$ and 1,25-dihydroxy-16-ene-23-yne cholecalciferol.

Compositions suitable for use in the claimed method include as an active agent a growth factor, Vitamin $D_3$ (or a metabolite or analog thereof) or a combination of both. Such compositions can be formulated by combining an active agent together with a pharmaceutically acceptable vehicle (carrier, diluent or excipient), in an amount sufficient to effect the preventative effect when administered in accordance with an appropriately designed treatment protocol. The composition can be in dosage unit form.

Though not limiting the present method to a particular mode of action, it is suggested that Vitamin $D_3$ protects against alopecia by increasing the receptors for EGF at the hair follicle level. Accordingly, administering a combination of a growth factor and Vitamin $D_3$ can be expected to provide for greater protection.

Compositions suitable for use in the method to which the invention relates can be in a form suitable for topical administration. In that event, the composition can take the form of a solution, lotion, cream, gel or ointment. When the composition is to be administered by injection, it advantageously takes the form of a solution. The vehicle used, regardless of the form taken by the composition, can be inert or can itself possess a physiologically or pharmaceutically beneficial effect.

Various additives can be included in the composition. In this regard, inclusion in the composition of an agent that stimulates production of the patients' own growth factor is contemplated. Inclusion in compositions suitable for topical administration of penetration enhancing agents, such as DMSO or ethanol, is preferred. Stabilizers that extend shelf life can also be included in the composition, regardless of the manner in which it is formulated.

One skilled in the art will appreciate that various concentrations of growth factor and/or Vitamin $D_3$ can be used in the above-described composition. Optimum concentrations can be readily determined by one skilled in the art.

As noted above, the method to which the invention relates can involve either topical application of the active agent (a growth factor and/or Vitamin $D_3$ or metabolite thereof) or administration by injection. The amount of the active agent and the frequency of administration can vary depending on the individual and can readily be optimized by one skilled in the art. As an example, however, a solution of 2–100 μg/ml of 1,25-dihydroxyvitamin $D_3$ in absolute ethanol can be prepared and 3–5 ml of that solution applied directly to the scalp at various points with a dropper followed by scalp message for 3–5 min to ensure even distribution. When chemotherapy is involved, this treatment is, advantageously, administered once or twice daily beginning 5–8 days prior to initiation of chemotherapy and continued through the course of chemotherapy. However, it is also contemplated that the active agent can be administered substantially simultaneously with, or subsequent to, the administration of the chemotherapeutic agent.

The method to which the invention relates is shown in the Examples that follow to be effective when the cell cycle specific drug, ARA-C, is the chemotherapeutic agent used and when the combination of Adriamycin (cell cycle specific) and Cytoxan (non cell cycle specific) is used. It is contemplated, however, that, using the present method, hair loss resulting from treatment with other chemotherapeutic agents can be prevented.

The alopecia preventative effect observed by Applicants was wholly unexpected. Growth factors, such as EGF, are presumed stimulants of skin cell growth. Accordingly, these agents would be expected to induce the hair follicle to enter the cell cycle thus rendering the follicle more susceptible to chemotherapeutic agents, particularly cell cycle specific drugs, such as ARA-C. Thus, administration of growth factors to patients receiving chemotherapy would have been expected to aggravate hair loss. The reverse effect, however, was achieved. It should be noted therefore that the observations recorded herein with EGF and FGF are novel and have not been proposed or described in the literature. Similarly, nothing about the role of Vitamin $D_3$ in the body suggested that the vitamin would provide such excellent protection against alopecia, chemotherapeutically induced or otherwise.

The following non-limiting Examples describe certain aspects of the invention in greater detail.

EXAMPLES

The following experimental details relate to Examples I–IV set forth below.

Sprague Dawley rats were purchased from Charles River Laboratories, Wilmington, Mass. Cytosar-U (ARA-C) was from the Upjohn Company, Kalamazoo, Mich. Receptor grade EGF from mouse submaxillary glands, human recombinant EGF, dimethyl sulfoxide (DMSO) and Vitamin $D_3$ were purchased from Sigma Chemical Co., St. Louis, Mo. aFGF was purchased from AMGEN Corp., Thousand Oaks, Calif.

All rats from each experiment were treated with ARA-C 50 mg/kg intraperitoneally (i.p.) daily for 7 days. For subcutaneous (s.c.) injections, EGF and FGF were prepared in PBS 1% BSA. Alopecia was always recorded on day 12 of experiment, and scored as previously described (Hussein et al, *Science,* 249:1564–1566, 1990; Jimenez et al, *FASEB J.*, 1991).

For topical treatment, murine EGF was prepared as follows: One vial of EGF (100 µg) was dissolved in 0.2 ml of PBS 1% BSA and 0.12 ml of this solution was added to 0.48 ml of DMSO. Three hours prior to ARA-C injection, 0.1 ml of the EGF-DMSO mixture was applied to each rat over a 1 $cm^2$ area between the shoulders using a rubber tip applicator. Rats were then kept individually separated for a period of three hours, following which the treated area was carefully washed with soap and water and dried. Treatment was continued for 7 days. Control animals were similarly treated using DMSO without EGF.

Example I

Protective Effect of EGF

Two separate experiments were conducted to test the ability of murine EGF to protect from ARA-C-induced alopecia. In Experiment I, twenty-two 7-day old rats were randomized in two groups of eleven rats each. In addition to ARA-C, Group I received 2 µg of mouse EGF s.c. in the back between the two hind legs 3 hours prior to ARA-C injections daily for 7 days. Group II, received buffer solution similarly and served as control. Ten of eleven rats in Group II developed virtually total body alopecia and one rat developed more than 50% hair loss. In contrast, in Group I, 5 rats had no detectable hair loss and 6 rats had mild hair loss (Table I, Experiment I (FIG. 1)). In Experiment II, twelve 7-day old rats were randomized in two groups of 6 rats each. In addition to ARA-C, Group I received mouse EGF 1 µg s.c. daily for 7 days. Group II received buffer s.c. All 6 rats in Group II developed moderately severe to severe alopecia, whereas in Group I, one rat had no detectable hair loss and 5 rats developed only minimal hair loss (Table I, Experiment II).

Figure 2:
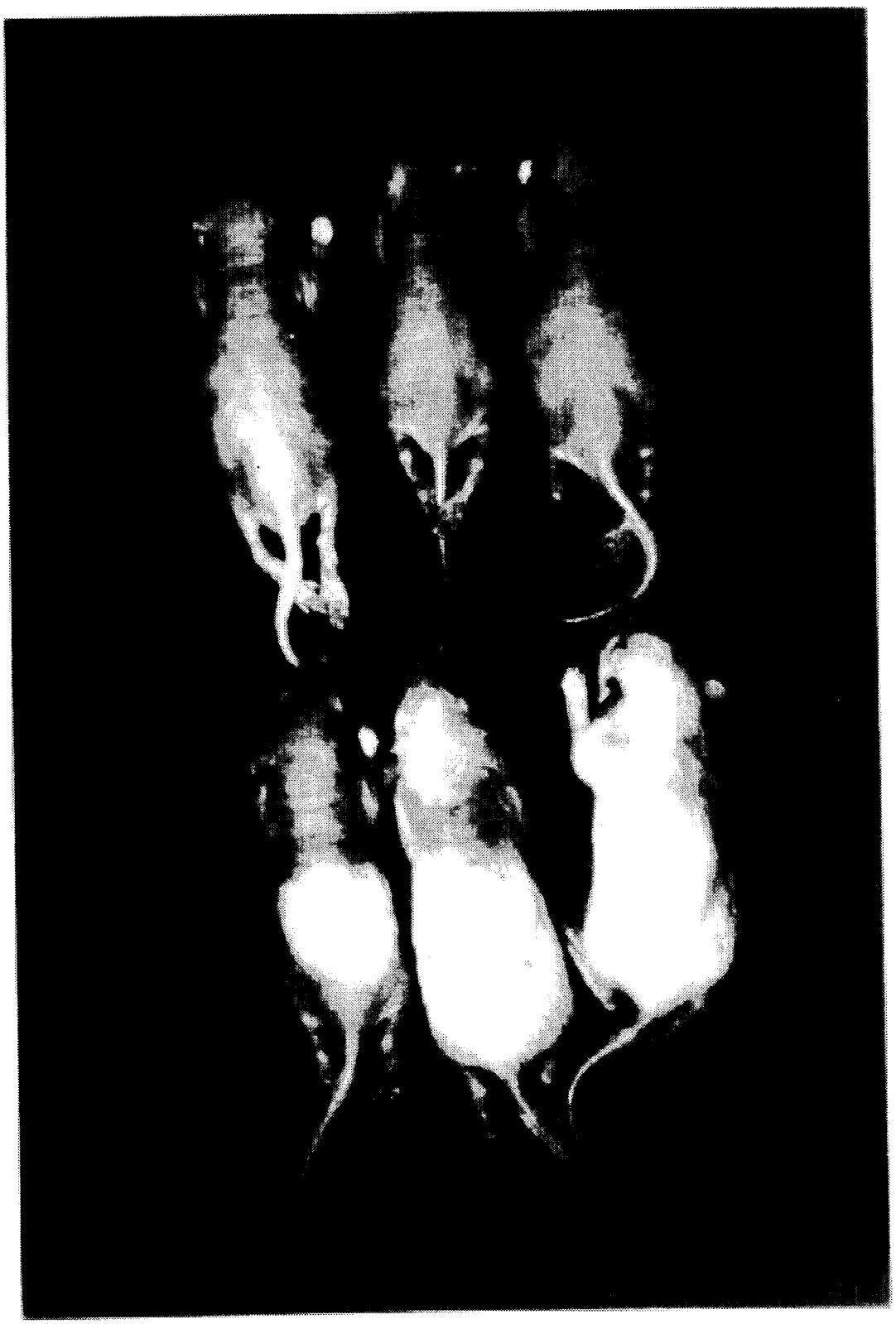
FIG. 2 is a photograph of 6 rats from Experiment III, Table I (see below). All rats received ARA-C 50 mg/kg×7 days. Three rats on top received buffer solution S.C. Three rats on bottom received rHu-EGF 2 µg s.c. daily×7 days.

For the next experiment, rHu-EGF was used. Twelve 7-day old rats were randomized in two groups of six rats each. In addition to ARA-C, Group I received rHu-EGF 2 µg s.c. in the flank area daily for 7 days. Group II received buffer s.c. All 6 rats in Group II developed total body alopecia, whereas in Group I none of the rats had total body alopecia, one rat had no detectable hair loss, four rats had mild alopecia and one rat had moderate alopecia (Table I, Experiment III, (FIG. 2)).

TABLE I

OCCURRENCE OF ALOPECIA IN RATS TREATED WITH ARA-C. EFFECT OF MURINE EGF AND rHU-EGF.

| | Alopecia* | | | |
|---|---|---|---|---|
| | 0 | 1+ | 2+ | 3+ |
| Experiment I | | | | |
| ARA-C | 0 | 0 | 1 | 10 |
| ARA-C + Murine EGF 2 µg | 5 | 6 | 0 | 0 |
| Experiment II | | | | |
| ARA-C | 0 | 0 | 3 | 3 |
| ARA-C + Murine EGF 1 µg | 1 | 5 | 0 | 0 |
| Experiment III | | | | |
| ARA-C | 0 | 0 | 0 | 6 |
| ARA-C + rHu-EGF 2 µg | 1 | 4 | 1 | 0 |

Seven day old rats were used for all experiments,
All rats received ARA-C 50 mg/kg × 7 days I.P. in 0.1 ml.
Murine EGF and rHu-EGF in PBS 14 BSA were given 3 hours prior to ARA-C once daily in 0.1 ml s.c. × 7 days.
Controls received PBS 1% BSA 0.1 ml s.c. × 7 days.
Data recorded on day 12.

*No detectable alopecia, 0; mild alopecia defined as less than 50% hair loss, 1+; moderately severe alpopecia with more than 50% hair loss, 2+; and total or virtually total (>90%) hair loss, 3+.

Figure 3:
FIG. 3 is a photograph of 4 rats from topical murine-EGF experiment (see below). All rats received ARA-C 50 mg/kg×7 days. Two rats on the left received murine EGF 10 µg in DMSO daily×7 days rubbed topically between the shoulder blades over an area of 1 cm². Two rats on the right received buffer solution topically.

In the next experiment, twelve 7-day old rats were randomized in two groups of six rats each. Group I, in addition to ARA-C, received murine-EGF 10 µg in DMSO daily×7 days rubbed topically with a cotton tip applicator between the shoulder blades over an area of 1 $cm^2$. Group II received control solution topically. In Group II, all six rats developed complete body alopecia. In Group I, all rats developed complete body alopecia except where the EGF was applied topically (FIG. 3).

Example II

Protective Effect of aFGF

Figure 4:
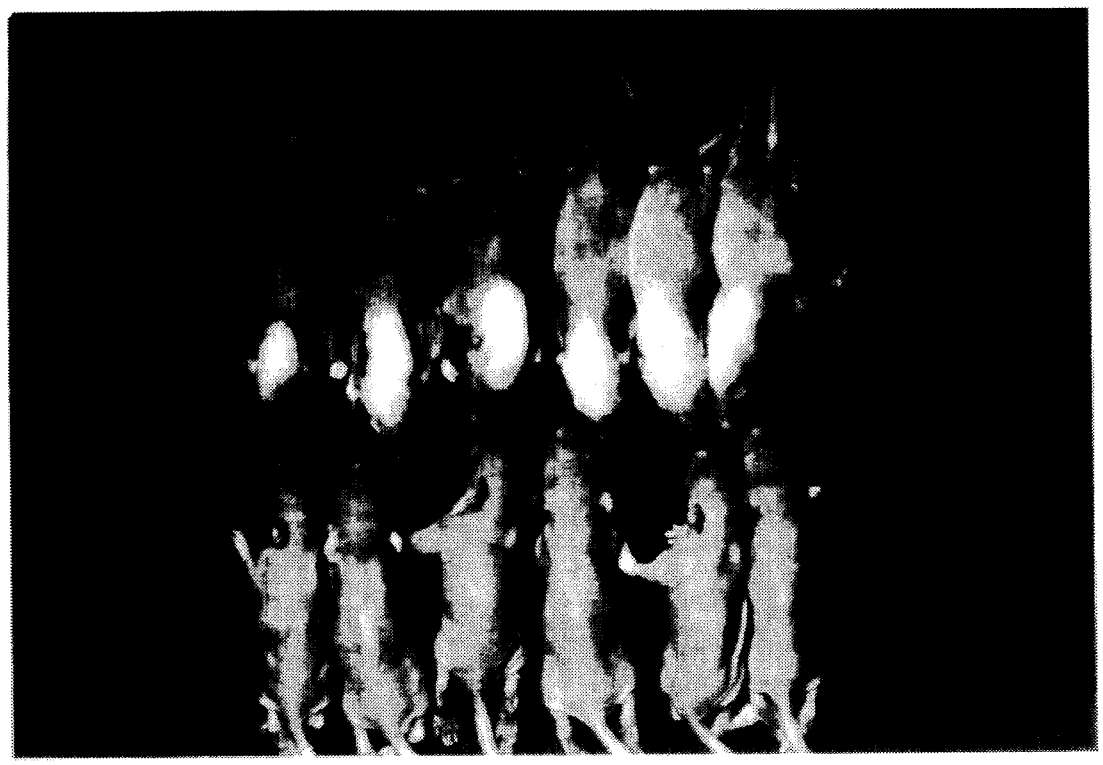
FIG. 4 is a photograph of 12 rats from ARA-C-aFGF experiment (see below). All rats received ARA-C 50 mg/kg×7 days. Six rats on top received buffer solution s.c. Six rats on bottom received aFGF 2 µg s.c. daily×7 days.

Fourteen 7-day old rats were randomized in two groups. All rats received ARA-C 50 mg/kg/day for seven days. In addition, Group I received aFGF 2 µg s.c. on back of head daily for seven days. Group II received buffer injections and served as controls. Alopecia was recorded on day 12 of experiment. All rats in Group II developed complete body alopecia. In contrast, all rats in Group I were protected locally at the site of injection (FIG. 4).

Example III

Protection from Cytoxan/Adriamycin-Induced Alopecia

Figure 5:
FIG. 5 is a photograph of 8 rats treated with combination chemotherapy Cytoxan and Adriamycin. Four rats on top treated in addition with murine EGF. Four rats on bottom treated with buffer solution.

Eight 4-day old Sprague Dawley rats were randomized in two groups of 4 rats each. Group I, received EGF 2µ s.c. on the head daily for 7 days. Group II received buffer injections and served as controls. One day after stopping EGF or buffer injections all rats received Cytoxan 25 mg/kg i.p.×1 day and Adriamycin 2.5 mg/kg i.p.×3 days. In Group II, all rats had 3+ alopecia over head and neck area. In contrast, in Group I one rat had mild alopecia, one rat minimal alopecia, and two rats no detectable alopecia over head and neck. (FIG. 5). ImuVert when used under similar conditions did not protect from alopecia caused by the Cytoxan/Adriamycin combination.

Example IV

Protective Effect of Vitamin $D_3$

Figure 6:
FIG. 6 is a photograph of 10 rats treated with VP-16. All rats received 1.5 mg/kg×3 days i.p. of VP-16. Five rats on top received buffer solution for four days prior to treatment. Five rats on bottom received Vitamin $D_3$ 50 µg/day for 4 days for four days prior to treatment.

Twelve 7 day old rats were randomized in two groups. Group I was treated daily with buffer 0.1 ml s.c. for four days. The second Group was treated daily with Vitamin $D_3$ 50μg s.c. over head for four days. After stopping the buffer or Vitamin $D_3$ treatment, all rats received 1.5 mg/kg i.p. of VP-16 (Etoposide) daily for three days. All rats in Group I developed complete body alopecia while the rats in Group II were protected (FIG. 6 shows 4 rats from each group).

Figure 7:
FIG. 7 is a photograph of 6 rats treated with combination chemotherapy Cytoxan and Adriamycin (25 mg/kg i.p.×1 day and 2.5 mg/kg i.p.×3 days, respectively). Three rats on top received buffer solution for four days prior to treatment. Three rats on bottom received Vitamin $D_3$ 50 µg/day for four days prior to treatment.

In other experiments, rats pretreated with Vitamin $D_3$ demonstrated excellent protection against alopecia produced by Etoposide, Cytoxan, Cytarabine and the combination of Cytoxan and Adriamycin (FIG. 7). The results are set forth below in Table II.

TABLE II

PROTECTION FROM CHEMOTHERAPY-INDUCED ALOPECIA BY PRETREATMENT WITH VITAMIN $D_3$.

| Alopecic drug tested | Total No. of experiments | Total No. of animals | Protection from alopecia |
|---|---|---|---|
| Etoposide (VP-16) | 2 | 22 | Yes* |
| Cytoxan (CTX) | 7 | 89 | Yes* |
| Cytarabine (ARA-C) | 1 | 8 | Yes* |
| Adriamycin + CTX Combination | 6 | 77 | Yes* |

Chemotherapeutic agents were given as follows: VP-16 1.5 mg/kg i.p. daily for 3 days; Cytoxan 32.5 mg/kg as a single injection; ARA-C 50 mg/kg i.p. daily for 7 days; for combination (Adriamycin 2.5 mg/kg i.p. daily for 3 days plus Cytoxan 25 mg/kg as a single injection). Vitamin $D_3$ was given in 50 μg daily doses i.p. or s.c. for 4 days prior to chemotherapy.

*In these experiments, protection from chemotherapy-induced alopecia was uniformly observed in all animals treated with Vitamin $D_3$ In other experiments, 1,25-dihydroxyvitamin $D_3$ applied topically (0.5 μg daily) in 50% ethanol or DMSO also protected rats from VP-16-induced alopecia.

Example V

Protective Effect of Vitamin $D_3$ Pretreatment

Topical Application of 1,25-dihydroxyvitamin $D_3$:

1,25-Dihydroxyvitamin $D_3$ was dissolved in absolute ethanol and applied topically with an applicator. Control animals were similarly treated with the same amount of ethanol. Animals were then kept individually separated for a period of three hours following which the treated area was carefully washed with soap and water and dried. Treatment was given daily beginning on day 5 after birth and ending on day 10.

Chemotherapy:

All chemotherapies were given I.P. and started at 11 days of age. CTX, 35 mg/kg, was given for one day only. VP-16, 1.5 mg/kg, was given for three days. For CTX and ADM combination, CTX, 25 mg/kg was given for one day and ADM, 2.5 mg/kg, for three days. At these doses neither CTX nor ADM alone will produce alopecia. Alopecia was recorded on the tenth day from beginning chemotherapy.

Figure 8A:
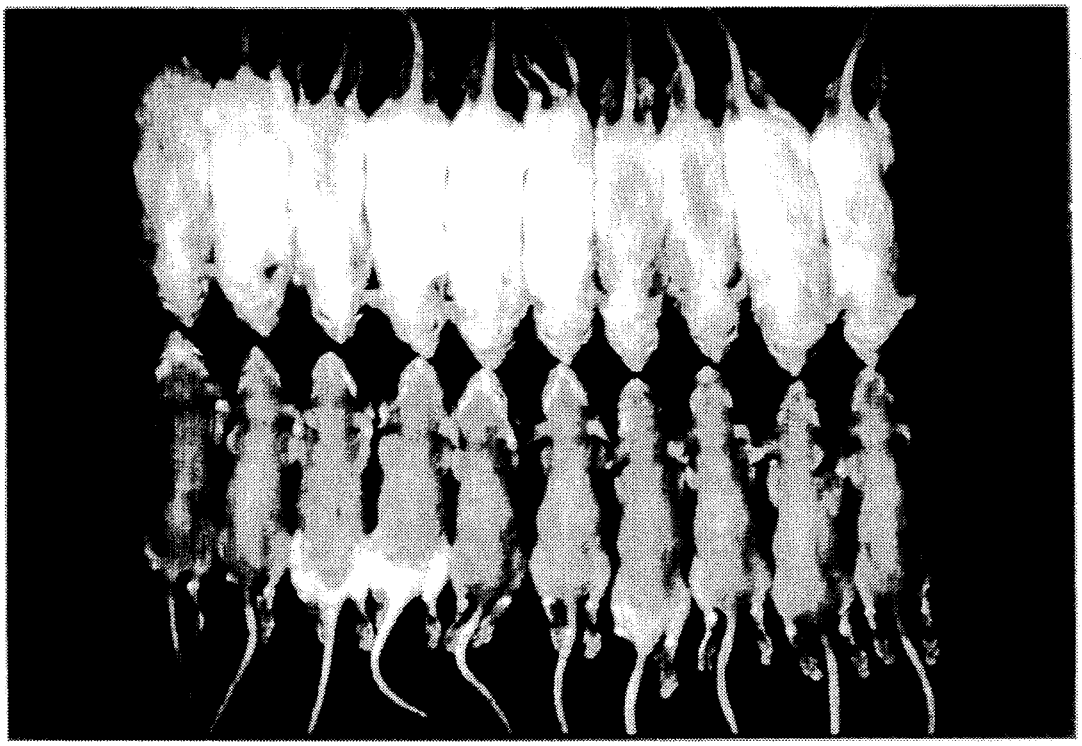
FIG. 8(A–C). For each experiment, five day old rats were randomly divided into equal numbers. The experimental group of rats (top group) received 0.2 µg of 1,25-dihydroxyvitamin $D_3$ in 0.15 ml of absolute ethanol daily over the head and neck for 5 days. Control rats (bottom group) were similarly treated with 0.15 ml of absolute ethanol. One day after the last topical treatment, the rats from FIG. 8A were treated with Cytoxan (CTX), rats from FIG. 8B with the Etoposide (VP-16) regimen and rats from FIG. 8C with CTX+Adriamycin (ADM) regimen.
Figure 8B:
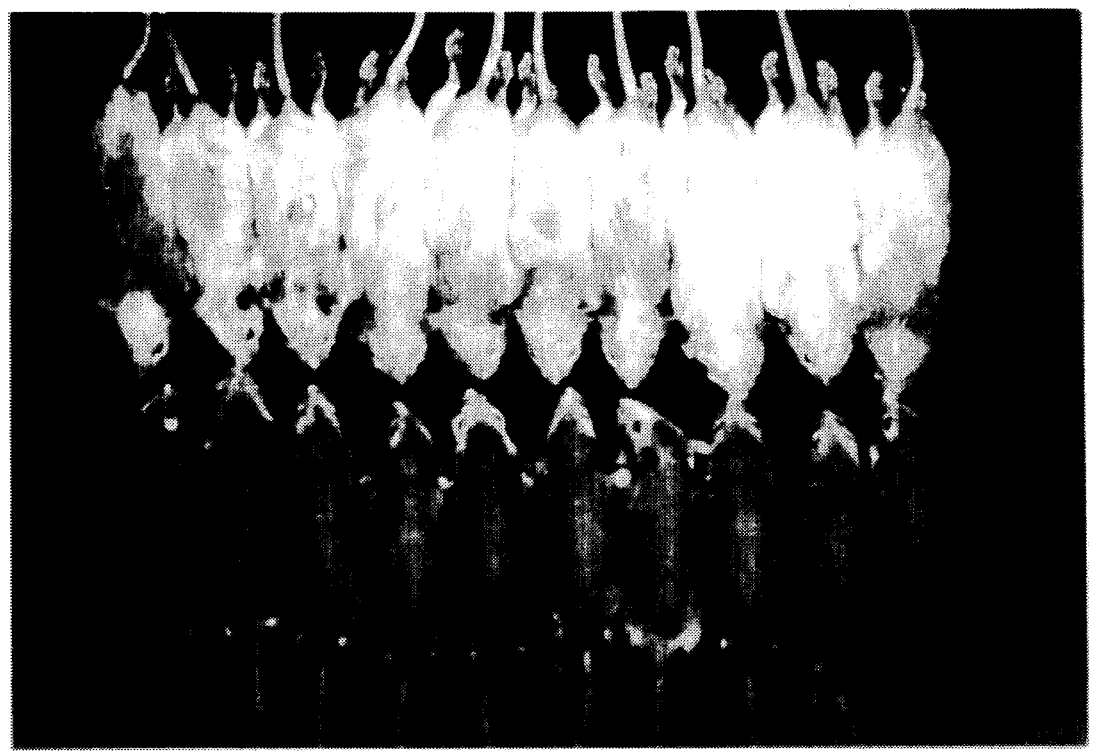
Figure 8C:
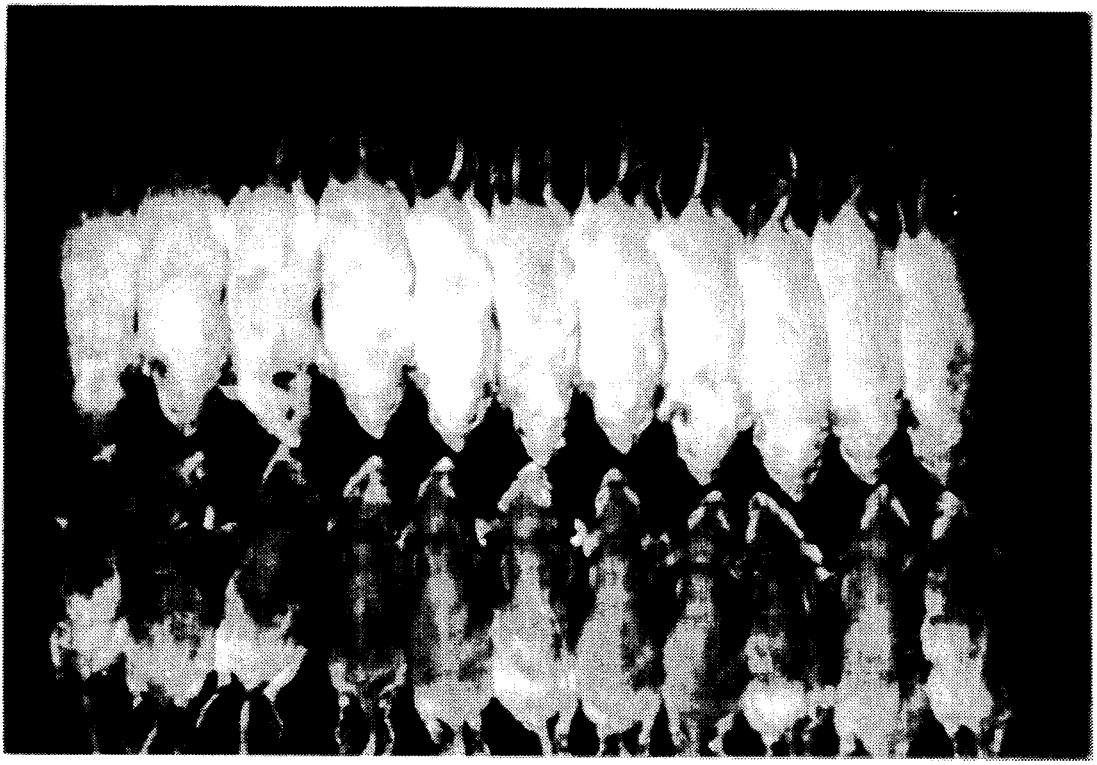
Figure 9:
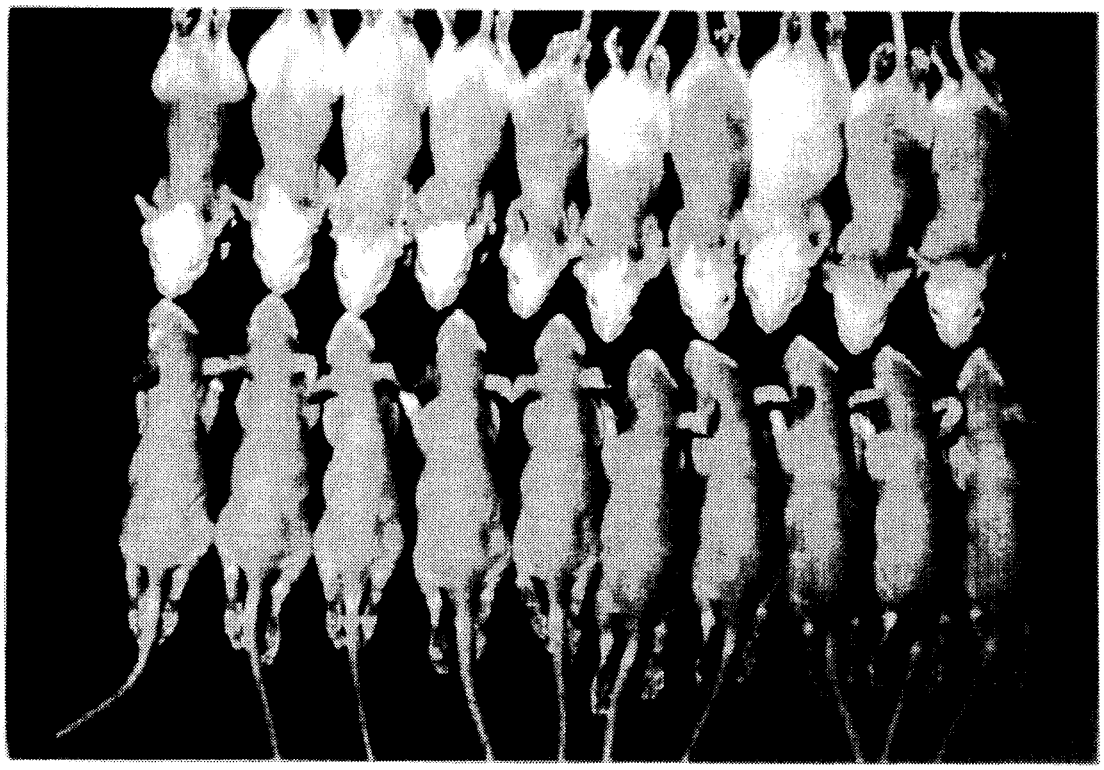
FIG. 9. Twenty 5-day old rats were randomly divided into two groups of 10 rats each. The experimental group of rats (top group) received 0.1 µg of 1,25(OH)2D₃ in 0.1 ml of absolute ethanol daily over the head only for 5 days. Control rats (bottom group) were similarly treated with 0.1 ml of absolute ethanol. One day after the last topical treatment, all rats were treated with the VP-16 regimen.

A total of 4 experiments were carried out. In the first experiment, protection from Cytoxan-induced alopecia was examined. The experimental group was pretreated with 0.2 μg of 1,25-dihydroxyvitamin $D_3$ in 0.15 ml of absolute ethanol applied topically over the head and neck and the control group received 0.15 ml of alcohol. All 10 rats in the control group became totally alopecic. In contrast, all animals in the experimental group were protected (FIG. 8A). The second experiment was carried out under similar conditions to examine protection from VP-16-induced alopecia. All 10 rats in the control group developed total body alopecia. In contrast, all rats in the experimental group were protected (FIG. 8B). The third experiment was designed to examine protection from alopecia induced by Cytoxan-Adriamycin combination. There were 11 rats in each group. Six rats in the control group developed alopecia over the head and neck and 5 rate developed total body alopecia. In contrast, all rats in the experimental group were protected (FIG. 8C). In the fourth experiment, protection from VP-16-induced alopecia was similarly examined except that the dose of 1,25-dihydroxyvitamin $D_3$ was reduced to 0.1 μg in 0.1 ml absolute ethanol applied topically over the head area only. All 10 rats in the control group became completely alopecic. In contrast, all rats in the experimental group were protected primarily at the site of 1,25-dihydroxyvitamin $D_3$ application (FIG. 9).

It is noteworthy that protection from 0.2 μg 1,25-dihydroxyvitamin $D_3$ was not limited to the site of application but involved the entire body, suggesting systemic absorption. When the dose was reduced to 0.1 μg applied to the head area only, protection from VP-16-induced alopecia was less generalized and was more limited to the site of application.

Example VI

Protection from VP-16-Induced Alopecia by Topical Application of RO 23-7553

RO 23-7553 (1,25 dihydroxy-16-ene-23-yne-cholecalciferol) was dissolved in absolute ethanol and applied topically with an applicator. Control animals were similarly treated with the same amount of ethanol. Animals were then kept individually separated for a period of three hours following which the treated area was carefully washed with soap and water and dried. Treatment was given daily beginning on day 9 after birth and ending on day 14.

On day 15 all animals received VP-16, 1.5 mg/kg i.p., for three days. Alopecia was recorded on day 25.

Figure 10:
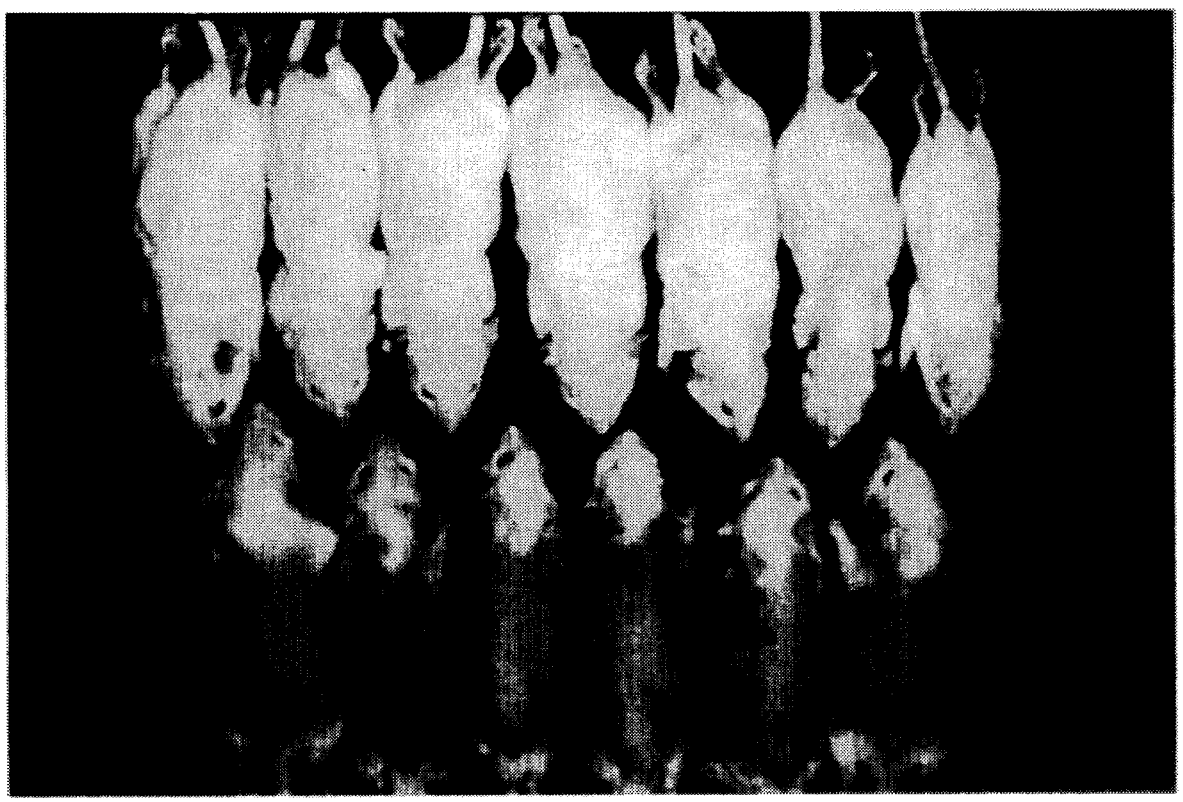
FIG. 10. Thirteen 9-day old rats were randomized into two groups. Experimental, 7 rats (top group), received 1 µg of RO 23-7553 in 0.2 ml absolute ethanol daily topically over the neck and back for 6 days. Control, 6 rats (bottom group), were similarly treated with 0.2 ml of absolute ethanol. One day after the last treatment all rats were treated with the VP-16 regimen.

Thirteen rats were randomized in two groups. Experimental group, 7 rats; control group, 6 rats. The experimental group was pretreated with 1 μg of RO 23-7553 in 0.2 ml absolute ethanol applied topically over the neck and beck and the control group received 0.2 ml of absolute ethanol. All six rats in the control group became totally alopecic over the neck and beck. In contrast, all animals in the experimental group were protected (FIG. 10). It should be noted that when the chemotherapy is started at the age of 14 days, the head area does not become alopecic.

Example VII

Stimulation of Hair Growth by Vitamin $D_3$

During the course of the above-described studies on the protection from chemotherapy-induced alopecia by Vitamin $D_3$ and its active analog, 1,25-dihydroxyvitamin $D_3$, it was noted that rats treated with 1,25-dihydroxyvitamin $D_3$ not only were protected from chemotherapy-induced alopecia, but these rats had a better coat of hair and longer hair in the treated area. These observations prompted the following further experiments on the stimulation of hair growth by 1,25-dihydroxyvitamin $D_3$.

The becks of nineteen 25 day old Sprague Dawley rats were shaven and randomized in two groups.

Group I (control 10 rats) received 0.1 ml of ethanol applied topically once daily to the shaven area for 14 days.

Group II (Calcitriol 9 rats) received 50 ng of 1,25-dihydroxyvitamin $D_3$ in 0.1 ml of ethanol applied topically once daily to the shaven area for 14 days.

Figure 11:
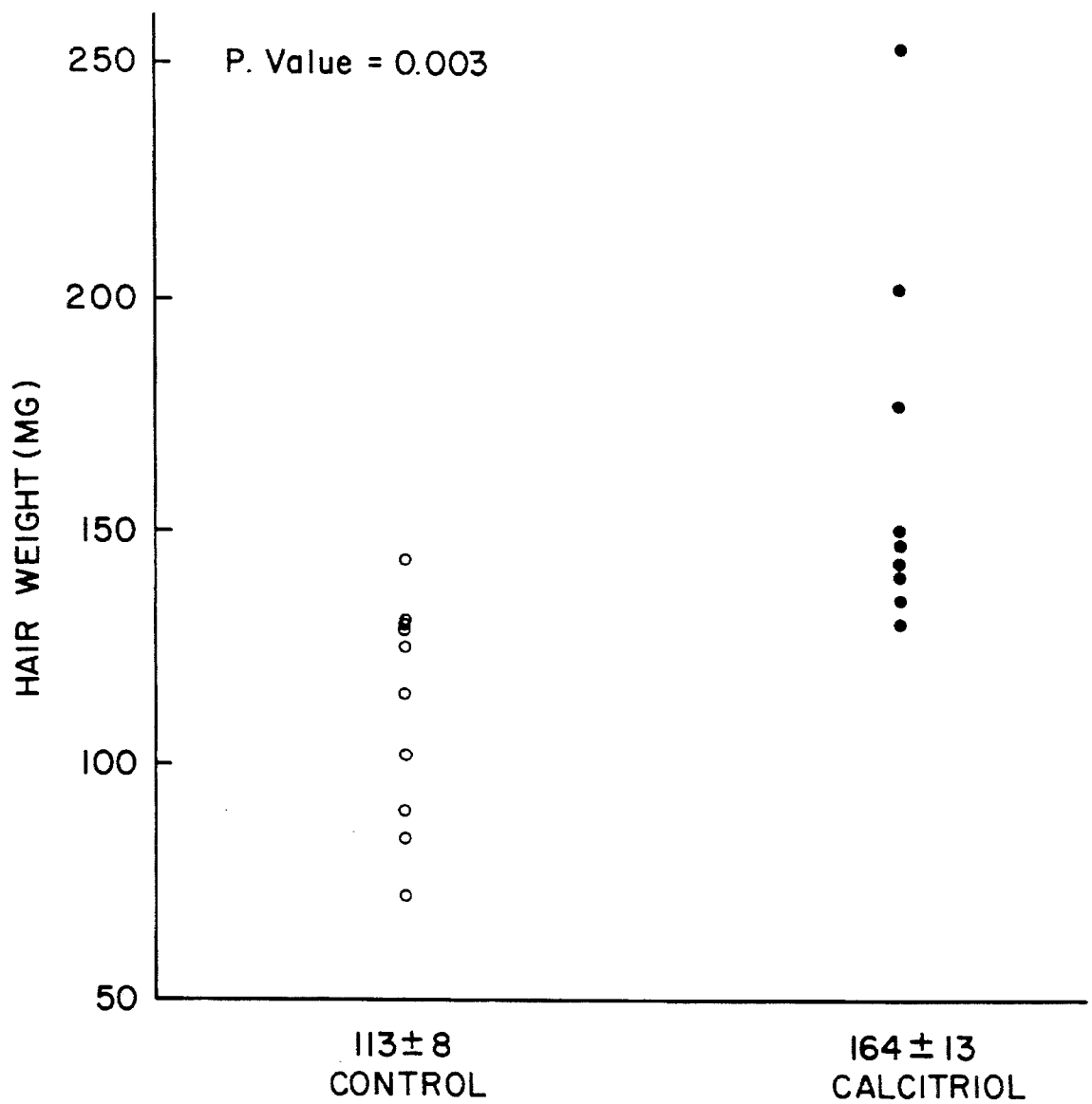
FIG. 11, shows the effect of 1,25-dihydroxyvitamin $D_3$ on hair growth.

On day 15 stimulation of hair regrowth was assessed by reshaving an area 6 cm×6 cm in diameter. The hair was collected and weighed. The difference between two groups was highly statistically significant. P. value 0.003 (see Table III and FIG. 11).

TABLE III

STIMULATION OF HAIR GROWTH BY CALCITRIOL IN RATS
Hair Weight in Mg.

| Control | Calcitriol |
|---------|------------|
| 98 | 202 |
| 131 | 143 |
| 72 | 150 |
| 84 | 253 |
| 102 | 130 |
| 144 | 177 |
| 115 | 140 |
| 129 | 147 |
| 125 | 135 |
| 130 | |
| Mean S.E.M. | Mean S.E.M. |
| 113 ± 8 | 164 ± 13 |

Based on these data showing stimulation of hair growth by 1,23-dihydroxyvitamin $D_3$ administered topically in the rat, it is expected that 1,25-dihydroxyvitamin $D_3$ can be used as a stimulant of hair growth in cases of alopecia of any cause. Additionally, the data suggest that vitamin $D_3$ and its metabolites is/are necessary for optimal hair growth and therefore can be used to prevent hair loss from any cause, including male pattern baldness.

Example VIII

Formulations

The following are four formulations that include 1,25-dihydroxyvitamin $D_3$ as active ingredient, and the methods of their manufacture.

1. TOPICAL SOLUTION

| Ingredients | % (W/W) |
|-------------|---------|
| 1,25-Dihydroxyvitamin $D_3$ | 0.0002–0.10 |
| Propylene Glycol | 10.00 |
| Propylene Glycol Dicarprylate/Dicaprate[a] | 30.00 |
| Butylated Hydroxytoluene (BHT) | 0.05 |
| Butylated Hydroxyanisole (BHA) | 0.05 |
| Ethyl Alcohol, Absolute q.s. to | 100.00 |

Manufacturing Procedure i. Weigh the appropriate amount of propylene glycol dicaprylate/dicaprate, ethyl alcohol, propylene glycol in a stainless steel container.
ii. Dissolve BHT and BHA into the solution from step (i).
iii. Add the 1,25-dihydroxyvitamin $D_3$ into the mixture from step (ii) and stir until dissolved.

2. BUFFERED TOPICAL SOLUTION

| Ingredients | % (W/W) |
|-------------|---------|
| 1,25-Dihydroxyvitamin $D_3$ | 0.0002–0.10 |
| Propylene Glycol | 50.00 |
| Hydroxypropyl cellulose (Klucel MF) | 0.50 |
| Methylparaben | 0.20 |
| Butylated Hydroxytoluene (BHT) | 0.05 |
| Butylated Hydroxyanisole (BHA) | 0.05 |
| Sodium Phosphate, Monobasic | 0.43 |
| Sodium Phosphate Dibasic | 0.70 |
| Sodium Hydroxide (q.s. to pH = 7) | 0.04 |
| Ethyl Alcohol, 95% Proof | 30.00 |
| Water q.s. to | 100.00 |

Manufacturing Procedure i. Dissolve the sodium phosphate, monobasic, sodium phosphate, dibasic, and sodium hydroxide in the water in a stainless steel container. Measure the pH of the solution. The pH of the solution should be 7.0; if not adjust the pH.
ii. Add the propylene glycol and ethyl alcohol to the solution from step (i).
iii. Dissolve the 1,25-dihydroxyvitamin $D_3$, methylparaben, BHT and BRA to the solution from step (ii).
iv. Dissolve Klucel MF to the solution from step (iii).

3. OIL-IN WATER BUFFERED TOPICAL LOTION

| Ingredients | % (W/W) |
|-------------|---------|
| 1,25-dihydroxyvitamin $D_3$ | 0.0002–0.10 |
| Cetyl Alcohol | 0.25 |
| Stearyl Alcohol | 0.50 |
| Sorbitan Monosterate | 2.00 |
| Glyceryl Monostearate and Polyoxyethylene Stearate Blend (Arlacel 165) | 4.00 |
| Polysorbate 60 | 1.00 |
| Mineral Oil | 4.00 |
| Propylene Glycol | 5.00 |
| Butylated Hydroxyanisole | 0.05 |
| Propylparaben | 0.05 |
| Buffering Agent q.s. to pH | 7.00 |
| Sorbitol Solution | 2.00 |
| Edetate Disodium | 0.10 |
| Methylparaben | 0.18 |
| Water q.s. to | 100.00 |

Manufacturing Procedure i. Prepare the buffer solution (pH 7.0) in a stainless steel container.
ii. In a stainless steel vessel, at 70° C., melt the cetyl alcohol, stearyl alcohol, sorbitan monostearate, Arlacel 165, Polysorbate 60, mineral oil, butylated hydroxyanisole, propylparaben, and 50% propylene glycol together.
iii. Add the sorbitol solution to step (i) and heat the solution to 70° C.
iv. Add the edetate disodium and methylparaben to the solution from step (iii).
v. Dissolve the 1,25-dihydroxyvitamin $D_3$ in approximately 40% propylene glycol in a beaker and add this to the material from step (ii) while mixing. Rinse the container from lot propylene glycol and add this to the mixture from step (ii).
vi. Add step (v) to step (iv) when both phases are at 70° C. and homogenize. Cool the emulsion to 200 m temperature.

4. TOPICAL GEL

| Ingredients | % (W/W) |
|-------------|---------|
| 1,25-dihydroxyvitamin $D_3$ | 0.0002–0.10 |
| Butylated Hydroxytoluene (BHT) | 0.05 |
| Butylated Hydroxyanisole (BRA) | 0.05 |
| Hydroxypropyl Cellulose | 3.00 |
| Ethyl Alcohol, 95% Proof | 50.00 |
| Water q.s. to | 100.00 |

Manufacturing Procedure i. Weigh the ethyl alcohol and water in a stainless steel container.

-continued ii. Dissolve the 1,25-dihydroxyvitamin $D_3$, BHT and BHA to the solution from step (i).
 iii. Dissolve the hydroxypropyl cellulose to the solution from step (ii).

<sup>a</sup>Can be substituted by the following materials (1) medium chain triglycerides; 2) dimethyl isosorbide; (3) polyethylene glycols; (4) ethoxydiglycol The entire contents of all references cited above are incorporated herein by reference.

While the present invention has been described in some detail for purposes of clarity and understanding, one skilled in the art will appreciate that various changes in form and detail can be made without departing from the true scope of the invention.

What is claimed is:

1. A method of reducing chemotherapy-induced alopecia comprising administering to a host treated with at least one chemotherapeutic agent which induces such alopecia an effective amount of vitamin $D_3$ or derivative or analog or active metabolite thereof.

2. The method according to claim 1 wherein said derivative, analog or active metabolite is selected from the group consisting of 1,25-dihydroxyvitamin $D_3$ and 1,25-dihydroxy-16-ene-23-yne-cholecalciferol.

3. The method according to claim 1 wherein said vitamin $D_3$, derivative analog or active metabolite thereof is administered topically.

4. The method according to claim 1 wherein said at least one chemotherapeutic agent is cell cycle specific.

5. The method according to claim 4 wherein said at least one chemotherapeutic agent is cytosine arabinoside.

6. The method according to claim 1 wherein said at least one chemotherapeutic agent is non-cell cycle specific.

7. The method according to claim 6 wherein said at least one chemotherapeutic agent is Cytoxan.

8. The method according to claim 1 wherein said at least one chemotherapeutic agent is a cell cycle specific agent in combination with a non cell cycle specific agent.

9. The method according to claim 1 wherein vitamin $D_3$, or derivative or analog or active metabolite thereof, is administered prior to the initiation of said chemotherapy.

10. The method according to claim 1, wherein the vitamin $D_3$, derivative or analog or active metabolite thereof is administered by topically applying the same to the host prior to administering said chemotherapy.

11. The method according to claim 1 wherein said derivative, analog or active metabolite is selected from the group consisting of 1,25-dihydroxyvitamin $D_3$ and 1,25-dihydroxy-16-ene-23-yne-cholecalciferol and is administered topically.

12. The method according to claim 1 wherein said at least one chemotherapeutic agent is cell cycle specific and said derivative, analog or active metabolite is selected from the group consisting of 1,25-dihydroxyvitamin $D_3$ and 1,25-dihydroxy-16-ene-23-yne-cholecalciferol.

13. The method according to claim 1 wherein said at least one chemotherapeutic agent is cell cycle specific and said vitamin $D_3$ or derivative, analog or active metabolite thereof is administered topically.

14. The method according to claim 1, wherein said at least one chemotherapeutic agent is cell cycle specific and comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1, 25-dihydroxyvitamin $D_3$.

15. The method according to claim 1 wherein said at least one chemotherapeutic agent is non cell cycle specific and said derivative, analog or active metabolite is selected from the group consisting of 1,25-dihydroxyvitamin $D_3$ and 1,25-dihydroxy-16-ene-23-yne-cholecalciferol.

16. The method according to claim 1 wherein said at least one chemotherapeutic agent is non cell cycle specific and said vitamin $D_3$ or derivative, analog or active metabolite thereof is administered topically.

17. The method according to claim 1 wherein said at least one chemotherapeutic agent is non cell cycle specific and comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1, 25-dihydroxyvitamin $D_3$.

18. The method according to claim 1 wherein said at least one chemotherapeutic agent is a cell cycle specific agent in combination with a non cell cycle specific agent and said derivative, analog or active metabolite is selected from the group consisting of 1,25-dihydroxyvitamin $D_3$ and 1,25-dihydroxy-16-ene-23-yne-cholecalciferol.

19. The method according to claim 1 wherein said at least one chemotherapeutic agent is a cell cycle specific agent in combination with a non cell cycle specific agent and said vitamin $D_3$ or derivative, analog or active metabolite thereof is administered topically.

20. The method according to claim 1 wherein said at least one chemotherapeutic agent is a cell cycle specific agent in combination with a non cell cycle specific agent and comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1, 25-dihydroxyvitamin $D_3$.

21. The method according to claim 1, wherein the vitamin $D_3$, or derivative or analog or active metabolite thereof is administered by topically applying the same to the host prior to administering said chemotherapy and said derivative, analog or active metabolite is selected from the group consisting of 1,25-dihydroxyvitamin $D_3$ and 1,25-dihydroxy-16-ene-23-yne-cholecalciferol.

22. The method according to claim 1, wherein the vitamin $D_3$, or derivative or analog or active metabolite thereof is administered by topically applying the same to the host prior to administering said chemotherapy and comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1, 25-dihydroxyvitamin $D_3$.

23. The method according to claim 1 comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$.

24. The method according to claim 1, comprising topically administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$.

25. The method according to claim 1, comprising topically administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$ and wherein said chemotherapeutic agent is cell cycle specific.

26. The method according to claim 1, comprising topically administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$ and wherein said at least one chemotherapeutic agent is non cell cycle specific.

27. The method according to claim 1, comprising topically administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$ and wherein said at least one chemotherapeutic agent is a cell cycle specific agent in combination with a non cell cycle specific agent.

28. The method according to claim 1, comprising administering vitamin $D_3$, 1,25-dihydroxy-16-ene-23-yne-cholecalciferol, 1α-hydroxyvitamin $D_3$, 1α, 24-dihydroxyvitamin $D_3$ or 1,25-dihydroxyvitamin $D_3$ prior to the initiation of said chemotherapy.

29. A method of reducing chemotherapy-induced alopecia comprising administering to a patient undergoing chemotherapy with at least one chemotherapeutic agent 1,25-dihydroxyvitamin $D_3$ in an effective amount.

30. The method according to claim 29 wherein said 1,25-dihydroxyvitamin $D_3$ is administered topically.

31. The method according to claim 29 wherein said at least one chemotherapeutic agent is cell cycle specific.

32. The method according to claim 31 wherein said at least one chemotherapeutic agent is cytosine arabinoside.

33. The method according to claim 29 wherein said at least one chemotherapeutic agent is non cell cycle specific.

34. The method according to claim 33 wherein said at least one chemotherapeutic agent is Cytoxan.

35. The method according to claim 31 wherein said at least one chemotherapeutic agent is a cell cycle specific agent in combination with a non cell cycle specific agent.

36. The method according to claim 31 wherein the 1,25-dihydroxyvitamin $D_3$ is administered prior to the initiation of said chemotherapy.

37. The method according to claim 31, wherein the 1,25-dihydroxyvitamin $D_3$ is administered by topical application to the host prior to administering said chemotherapy.

\* \* \* \* \*